United States Patent [19]
Tyndorf et al.

[11] Patent Number: 5,882,922
[45] Date of Patent: *Mar. 16, 1999

[54] CULTURE VESSEL ASSEMBLY

[75] Inventors: Tadeusz A. Tyndorf, Manalapan, N.J.; Timothy A. Stevens, Warwick, N.Y.; Susan L. Barker, Tenafly, N.J.

[73] Assignee: Becton Dickinson and Company, Franklin Lakes, N.J.

[*] Notice: The term of this patent shall not extend beyond the expiration date of Pat. No. 5,780,294.

[21] Appl. No.: 818,649

[22] Filed: Mar. 19, 1997

[51] Int. Cl.⁶ .................................................. C12M 3/00
[52] U.S. Cl. ................................. 435/305.3; 435/305.4; 435/325; 435/410; 215/258; 215/308; 220/371
[58] Field of Search ............................ 435/288.3, 305.1, 435/305.2, 305.3, 305.4, 325, 410; 215/248, 258, 261, 307, 308; 220/507, 550, 361, 363, 367.1, 371

[56] References Cited

U.S. PATENT DOCUMENTS

| | | | |
|---|---|---|---|
| 1,515,016 | 11/1924 | Earp-Thomas | 435/305.4 |
| 4,657,867 | 4/1987 | Guhl et al. | 435/284 |
| 5,358,871 | 10/1994 | Stevens et al. | 435/284 |
| 5,417,576 | 5/1995 | Hill | 435/305.4 |

FOREIGN PATENT DOCUMENTS

| 404158779 A | 6/1992 | Japan | 435/305.3 |
|---|---|---|---|

*Primary Examiner*—David A. Redding
*Attorney, Agent, or Firm*—Bruce S. Weintraub; Nanette S. Thomas

[57] ABSTRACT

A multiwell tissue culture assembly for culturing cells comprising a plate and a lid. The plate includes a plurality of wells for accommodating a cell culture insert and the lid includes means for varying the gas diffusion into and out of the assembly and for substantially minimizing biological contamination of the cells being cultured in the cell culture insert. The means for varying the gas diffusion is a gas permeable membrane provided in an opening in the lid and a removable thin impermeable film label is provided for selectively occluding passage of gases through the gas permeable membrane.

14 Claims, 7 Drawing Sheets

CULTURE VESSEL ASSEMBLY

BACKGROUND OF THE INVENTION

1. Field of the Invention

This invention relates to an apparatus and procedures for growing cells or tissue culture in vitro and more particularly to a culture vessel assembly having means for varying the gas diffusion rate into and out of the assembly and for substantially minimizing biological contamination of the cells or tissue culture in the assembly.

2. Description of Related Art

Culture vessels are described in U.S. Pat. Nos. 4,495,289, 5,026,649, 5,358,871 and 5,366,893 and European Patent Application No. 0 483 620 A2 and U.K. Patent Application No. GB 2 268 187 A. Culture vessels comprise wells which generally have a circular shape and size which permits the introduction therein of a cell culture insert having a membrane upon which cell attachment, growth and differentiation occur. The culture vessels containing the wells are typically rectangular and have a standard size in order to accommodate standard analytical apparatus. Cell culture inserts used in culture vessels are described in U.S. Pat. Nos. 4,871,674, 5,026,649 and 5,366,893 and are herein incorporated by reference.

The culture of cells is very dependent upon the ability to supply sufficient oxygen to the cells without causing cellular damage. The supply of oxygen for cell respiration is from the atmosphere in the header space above the cells via the liquid culture medium.

Aeration of the culture, by for example, sparging, surface aeration, medium perfusion, can increase the oxygen availability, however such methods can cause cellular damage. Silicone rubber tubing has been used to improve gas exchange in cell culture, by running the tubing between the well and the atmosphere, but this method is inconvenient and may cause contamination to the cell suspension.

Although there are a number of culture vessels commercially available and described in patent publications, it is believed that there are no culture vessels available that provide a means for varying the gas diffusion rate into and out of a culture vessel assembly while still providing a closed system whereby entry or exit of biological contaminants into or out of the vessel is substantially minimized.

SUMMARY OF THE INVENTION

The present invention is an assembly for growing cells or tissue culture in vitro. The assembly comprises a test plate with wells shaped to accommodate an insert, such as a cell culture insert, or for receiving tissue culture media and a removable lid.

The test plate preferably comprises an upper surface, a lower surface, and a plurality of wells. Each well is substantially disposed between the upper and lower surface of the test plate.

The assembly further includes a removable lid which can be positioned over the upper surface of the test plate. The lid includes a top wall and a peripheral skirt that extends downwardly from the top wall. The lid serves to prevent the loss of sample from the well interior, to protect the contents of the assembly from the environment and to protect the user from the contents of the assembly should it contain a harmful or potentially harmful material.

The test plate and related removable lid may be formed in different sizes and geometric configurations so as to be used with different size and geometric configured cell culture inserts. The removable lid may be formed to be positioned over the upper surface of the plate in one orientation so as to reduce cross contamination between the wells in the event the lid is repositioned over the upper surface of the plate. The plate and the removable lid are preferably made of an optically clear plastic to facilitate viewing of the wells and cell culture inserts.

Preferably, the lid comprises means for allowing gas diffusion into and out of the wells of the plate. Most preferably, the means for allowing the gas diffusion into and out of the wells of the plate is at least one port. Associated with the port is a gas permeable membrane. Most preferably, the gas permeable membrane is liquid impermeable.

Further associated with the lid is a means for selectively occluding the gas permeable membrane without removing the lid from the test plate. Preferably, the means for selectively occluding the membrane is a thin impermeable film. A thin film may be removably attached to the top of the lid over the port to restrict exposure of the gas permeable membrane to the atmosphere. The thin impermeable film assists is maintaining the biological security of the environment in the wells because the lid does not have to be lifted or removed from the test plate.

Most preferably, the means for selectively occluding the membrane is a peel-away gas impermeable label. Most preferably, the label is plastic. Preferred materials of the label, include but are not limited to polymeric substrate resins that are impermeable to gases and liquids. The label may be transparent or color coded. Moreover, the surface of the label may be such that additional information may be hand written on the label.

Although it is within the purview of the invention to provide a label that is circular, labels of different geometric configurations may be provided.

The label allows the user to control the exchange of gas in the test plate so that the desired growth of the cell culture can be facilitated in the test plate while still providing a closed system that prevents entry of microbial organisms or other contaminants into the wells of the test plate. The label substantially maximizes gas exchange while minimizing the possibility of contamination in the wells of the test plate. A further advantage is that gas exchange takes place exclusively through the membrane without having to partially open the lid and therefore the sterility and leakage into the assembly is substantially minimized.

The label does not compromise sterility or invite leakage into the test plate. Other advantages is that the label is reusable and is economically feasible to manufacture.

Most notably, the assembly of the present invention provides the following advantages: (1) a closed vented environment while maintaining sterility and controlling gas exchange; (2) containment of potentially hazardous samples; and (3) minimizing contamination of specimen in the assembly with environmental/exogenous contaminants such as yeast, bacteria and/or virus.

In addition, the present invention is particularly advantageous when culturing layers of cells, such as in skin cultures where it is desirable to produce layers of keratinocytes for skin grafting in a sterile and gas exchange controlled environment.

In addition, the present invention allows for the controlled passage of oxygen directly to the dividing cells which lie on the membrane surface of the cell insert.

In accordance with the principles of the assembly of the present invention, significant improvements over currently known and available multiwell tissue culture assemblies are provided. Most importantly, the present invention substantially improves gas diffusion into and out of the assembly while maintaining the sterility of the contents of the multiwell plate and allows adequate gaseous exchange to occur between the wells and the external environment. Accordingly, the assembly of the present invention provides a biologically closed environment so as to optimize conditions for cell culturing procedures whereby entry or exit of biological contaminants, gases and/or liquids is substantially minimized.

DETAILED DESCRIPTION

Figure 1:
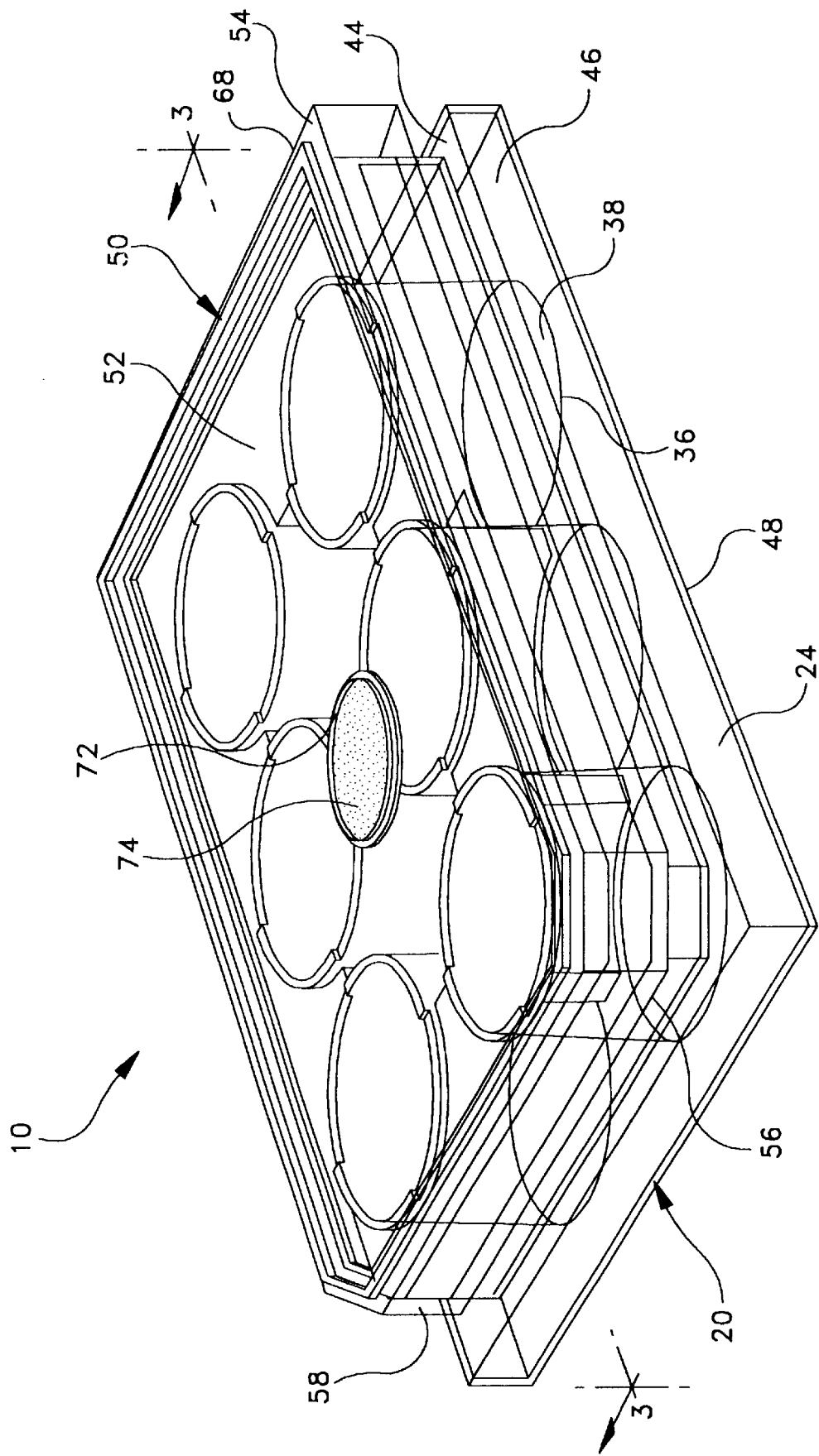
FIG. 1 is a perspective view of the assembly of the present invention.

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

Figure 2:
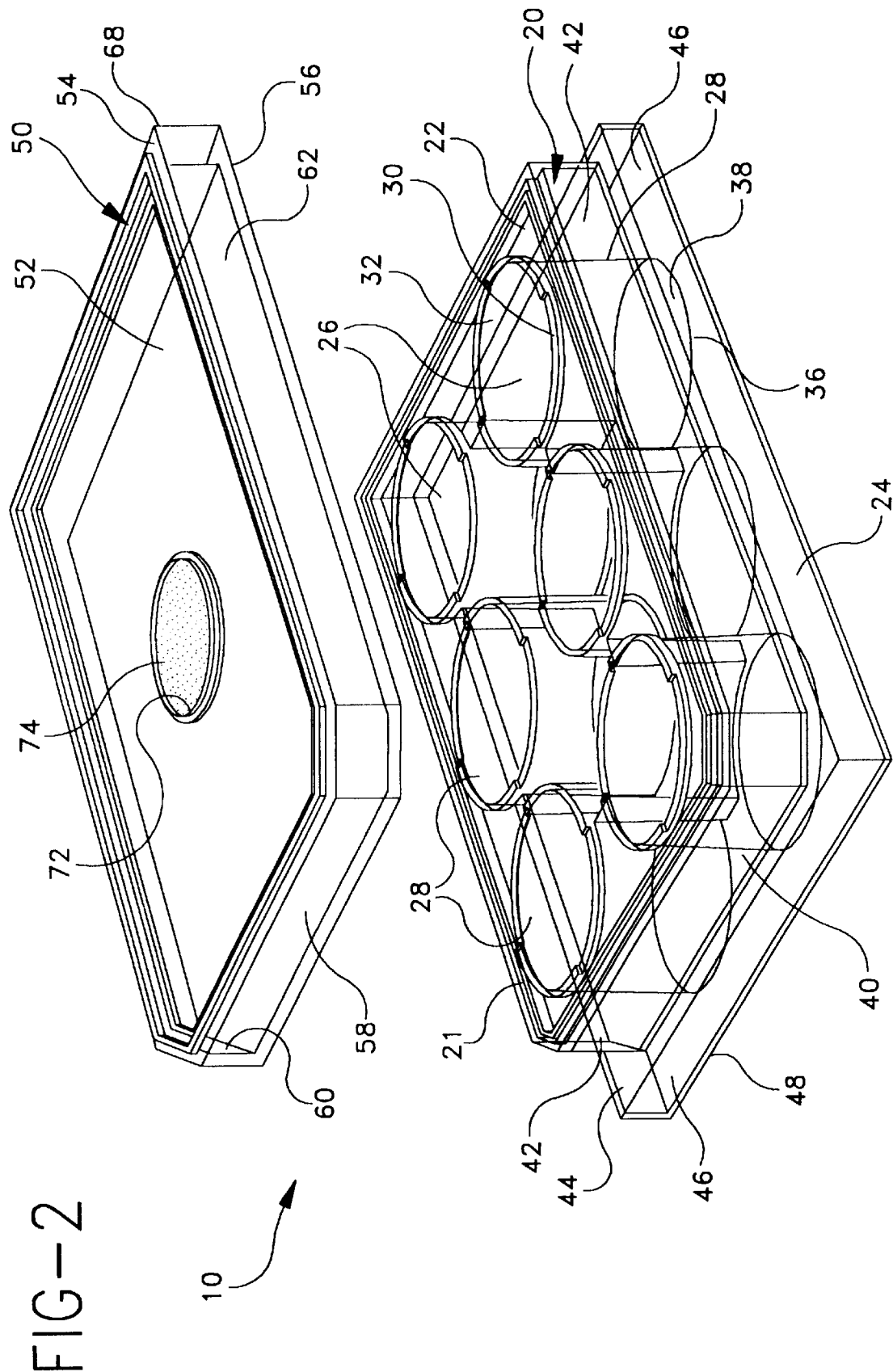
FIG. 2 is a perspective view of the assembly of the present invention with the lid removed.

An apparatus 10 for growing tissue culture as shown in FIGS. 1–2 includes a culture vessel plate 20 and a lid 50. As shown in FIG. 2 culture vessel plate 20 includes an upper surface 22 and lower surface 24. The culture vessel plate further includes a number of wells 26 each comprising a sidewall 28 extending from upper surface 22 of the plate to lower surface 24 of the plate. Each well comprises a top portion 30 and a bottom portion 36. Top portion 30 comprises an open end 32, that extends to bottom portion 36 that comprises a closed end 38.

There may be any number of wells 26 in plate 20, although six, twelve, twenty-four, forty-eight and ninety-six well plates are commonly known and available. In FIG. 1, a six-well plate is illustrated, merely for exemplary purposes. Most standard multiwell plates have the wells arranged in orthogonal rows and columns so as to be able to clearly identify the individual wells being used, of course, the arrangement of the wells in plate 20 is not an essential limitation of the present invention, since any arrangement of wells is contemplated by the invention.

Plate 20, as illustrated in the figures, typically is transparent and may be molded, for example, of polyvinylchloride or polystyrene.

Surrounding the wells and forming the outside border of plate 20 are sidewalls 40. In the present embodiment, plate 20 has six (6) sidewalls. Well known tissue culture plates are rectangle or quadrilaterally shaped, although for purposes of the present invention the plate may be fabricated in any practical configuration.

Figure 3:
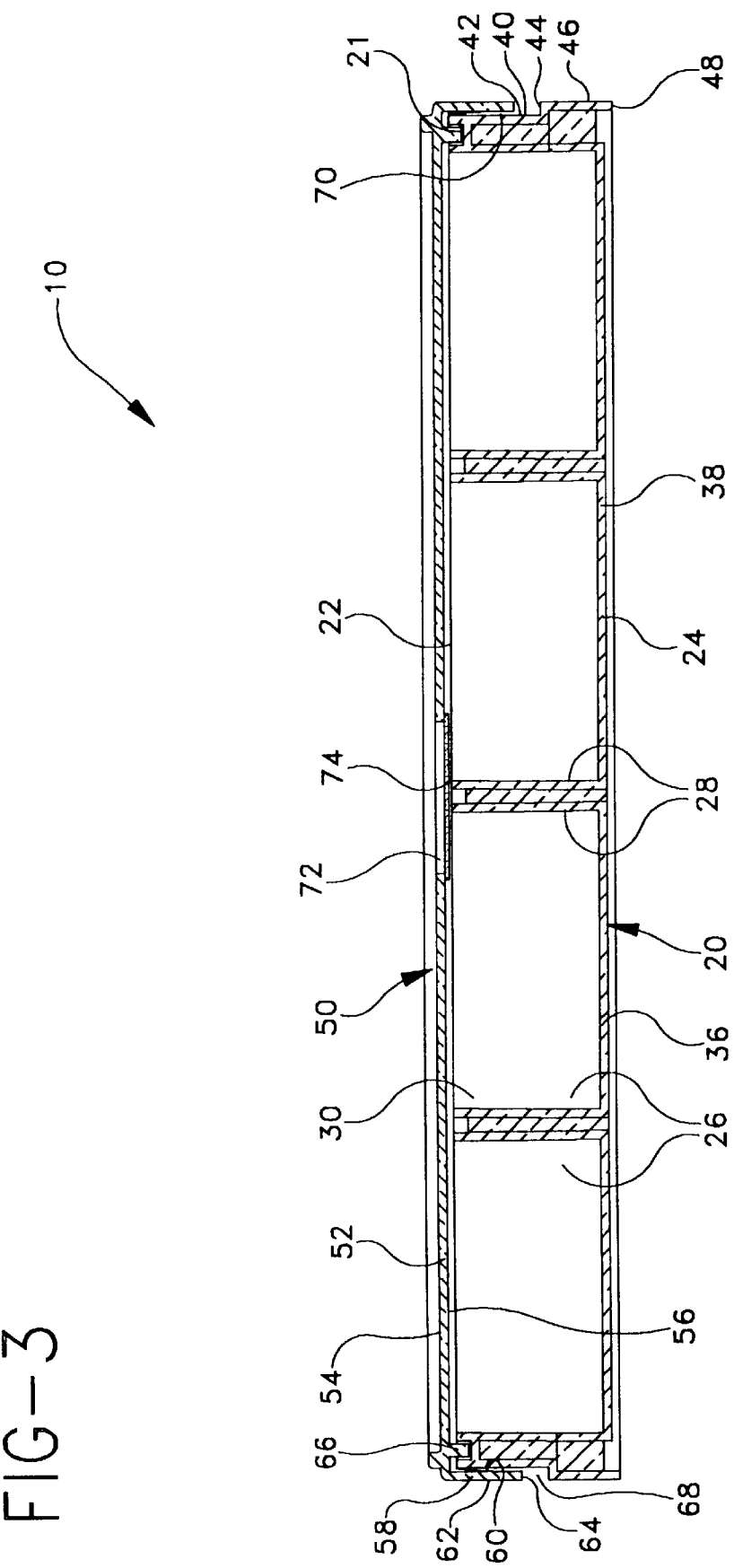
FIG. 3 is a cross-sectional view of the assembly taken along lines 3—3 of FIG. 1.
Figure 4:
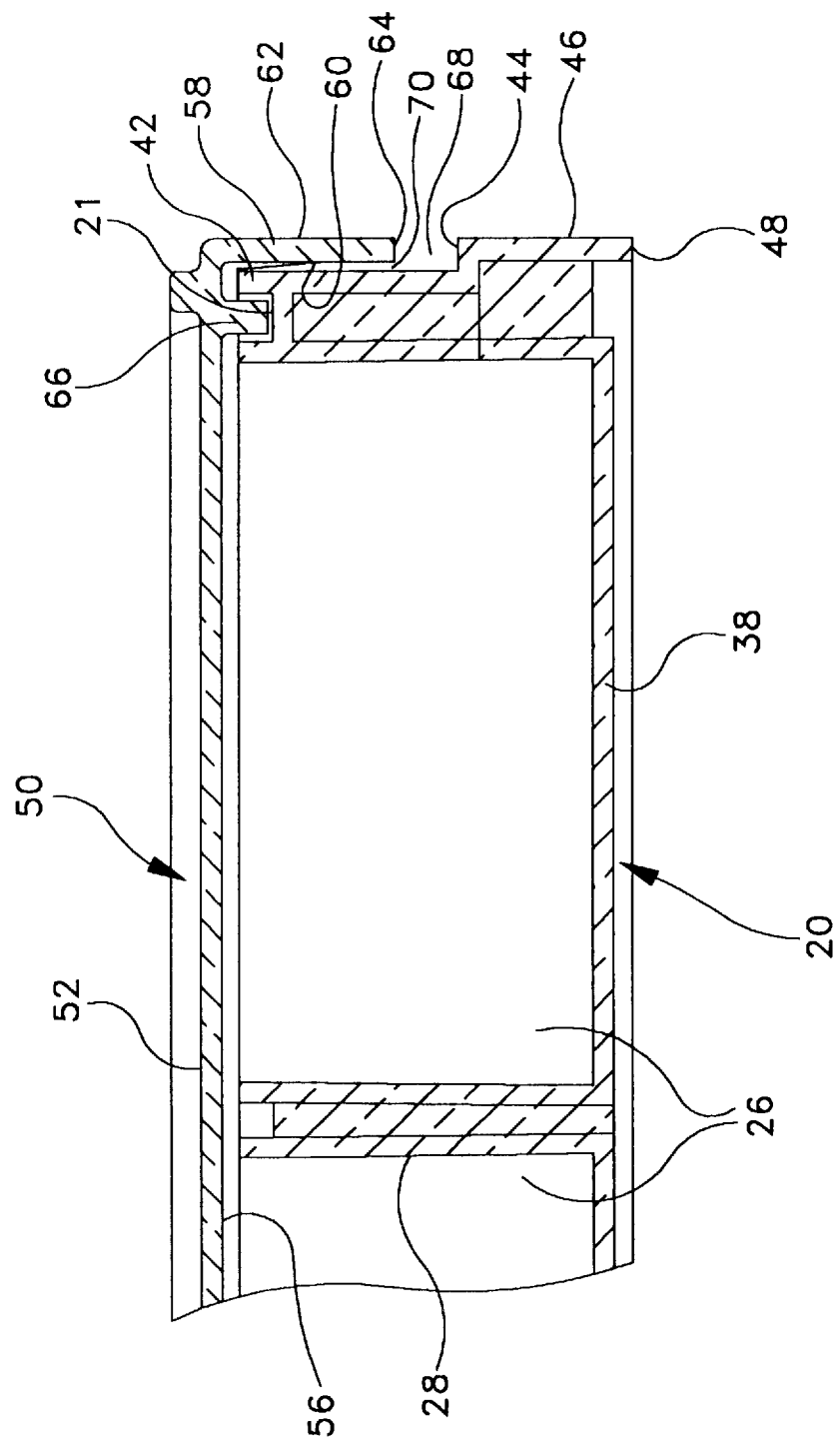
FIG. 4 is an enlarged, partial sectional view of the assembly of FIG. 3.

Spaced inwardly from sidewalls 40 of the plate and around the upper section of plate 20 is a recessed ledge 21 as more clearly seen in FIGS. 3 and 4 taken with FIGS. 1 and 2. Ledge 21 forms a border around the wells on the upper surface of plate 20 and wherein the sidewalls 40 extend to a position raised above the ledge thereby forming a rim surrounding the ledge.

Sidewall 40 comprises a two-step section comprising an upper section 42 and a lower section 46. Lower section 46 is stepped from upper section 42 by an annular shoulder 44 between the upper and lower sections. Therefore, upper section 42 extends from the upper surface 22 to an annular shoulder 44 and lower section 46 extends from annular shoulder 44 to bottom surface 48 of lower surface 24.

Lower section 46 serves as an annular base for plate 20 when the present multiwell tissue culture apparatus is being used.

Lid 50 is a separate, removable member which covers all of the wells of the plate. Although lid 50 is illustrated in all of the figures, the details of lid 50 are best illustrated in FIGS. 2–3. Lid 50 includes a substantially planar cover 52 large enough to extend over all of the wells of the plate planar cover 52 has a top surface 54 and a bottom surface 56. The shape of cover 52 is compatible with the shape of plate 20. Most preferably, as shown in FIG. 1, lid 50 is formed to be positioned over the upper surface of the plate in one orientation so as to reduce cross contamination between the wells in the event the user tries to reposition the lid over the plate.

Extending around cover 52 is a downwardly depending skirt 58 which forms a border around lid 50. Skirt 58 has an inner wall surface 60 and an outer wall surface 62, and six sides each of which extends downwardly from the cover to a bottom stop surface 64. Inwardly, spaced from skirt 58 and extending downwardly from bottom surface 56 of the planar cover is rib 66. This rib, lying substantially parallel to each of the sides of skirt 58 is positioned on the cover so as to depend downwardly into recessed ledge 21 in the plate.

Located on cover 52 is one orifice 72 as shown in FIGS. 1–3. A gas permeable, liquid impermeable membrane 74 is associated with the orifice as shown in FIGS. 1–3. Gas permeable membrane materials may be made from any suitable gas permeable material so long as it provides free passage of gases such as oxygen and carbon dioxide into the test plate while preventing microorganisms such as bacteria and fungi from passing there through.

As shown in FIG. 4, when lid 50 is positioned over plate 20, skirt 58 extends towards annular shoulder 44 of the plate thereby leaving a space 68 therebetween annular shoulder 44 and bottom stop surface 64. Moreover, as shown in FIG. 4, there is a second space 70 between inner wall surface 60 of skirt 54 and upper section 42 of the sidewall of the plate.

Figure 5:
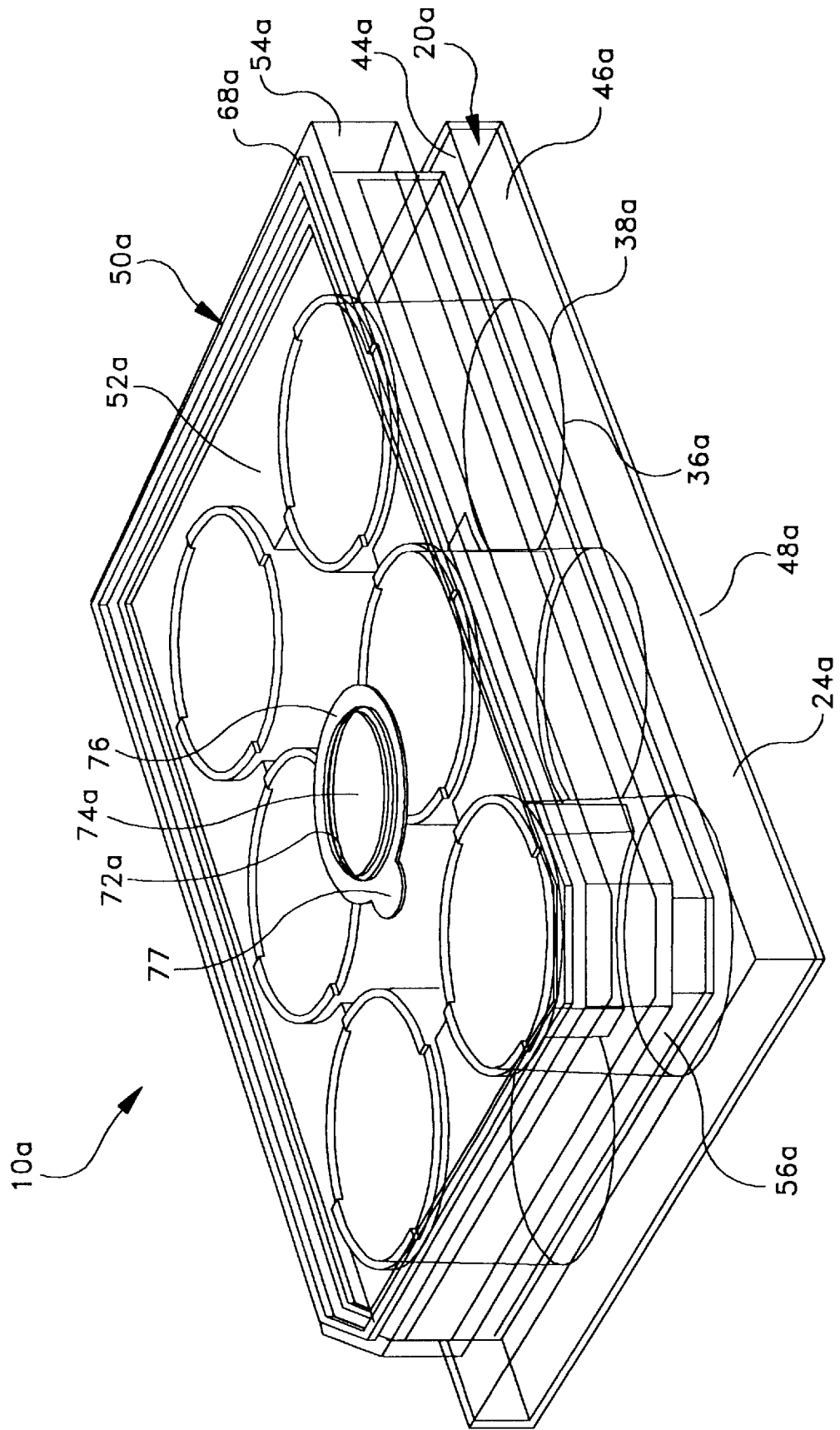
FIG. 5 is a perspective view of an alternate embodiment of the present invention with a label on the lid covering the orifice.

An additional embodiment of the invention as shown in FIG. 5 includes many components which are substantially identical to the components of FIG. 1. Accordingly, similar components performing similar functions will be numbered identically to those components of FIG. 1 except that a suffix "a" will be used to identify those similar components in FIG. 5.

As shown in FIG. 5, optionally a peel-away thin film label 76 is removably attached to cover 52a to selectively occlude membrane 74a of orifice 72a. The film may be fully or partially removed or left in place according to the particular culture requirements.

Conventional means are used to apply the peel-away thin film label to the cover. These means include adhesive materials such as pressure sensitive materials, wherein the thin film label can be easily partially or fully removed from the cover as is required and reapplied as needed. The thin film label material may be made of polyethylene or polyethylene terephthalate and adhesive materials may include acrylic adhesives.

As shown in FIG. 5, optional peel-away thin film label 76 is circular and has a tab 77 for ease of use. Although it is within the purview of the invention to provide a peel-away thin film that is circular, films of different geometries and dimensions may be provided.

Figure 6:
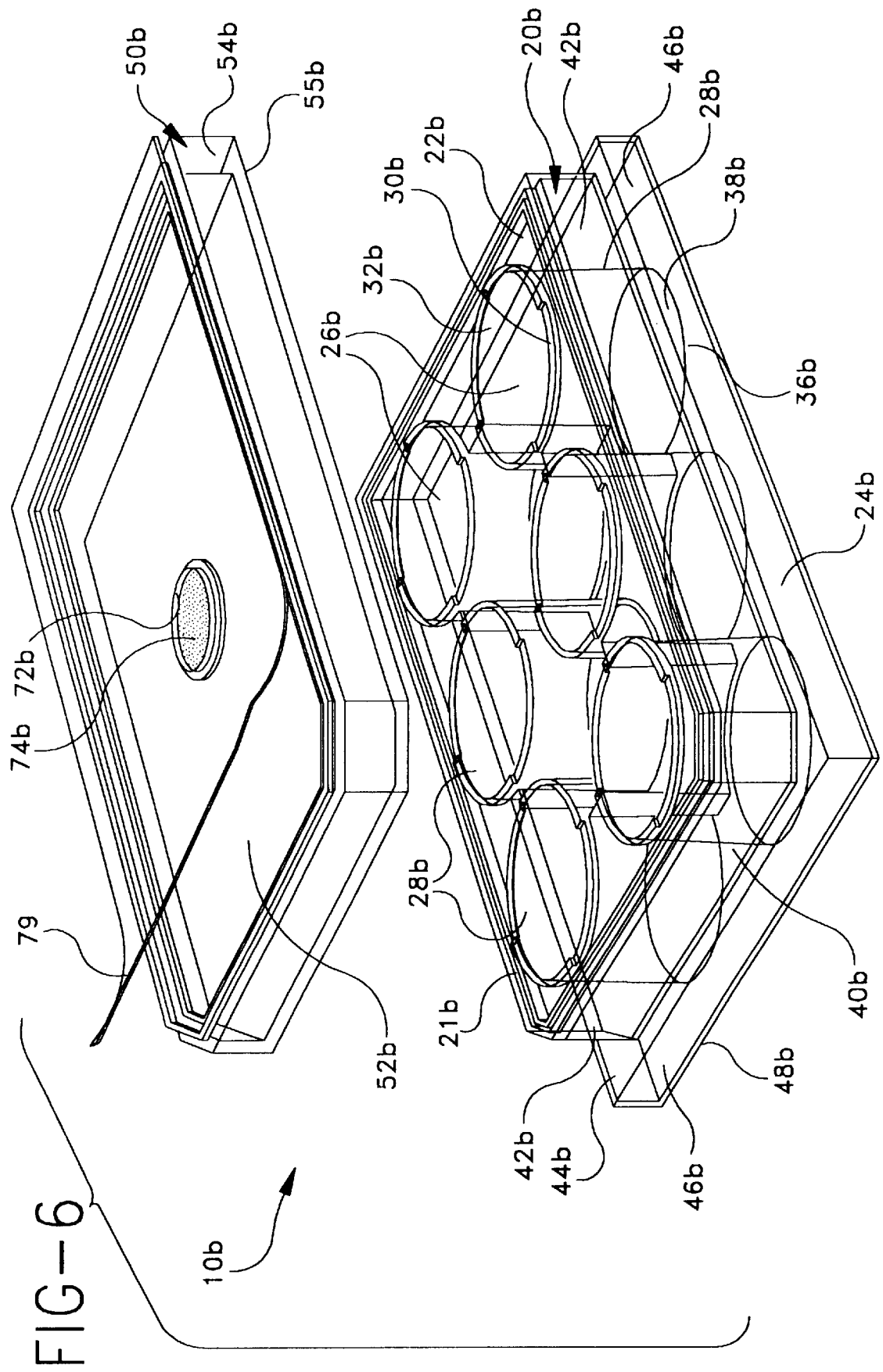
FIG. 6 is a perspective view of an alternate embodiment of the present invention with a label covering the entire lid.

An additional embodiment of the invention as shown in FIG. 6 includes many components which are substantially identical to the components of FIG. 2. Accordingly, similar components performing similar functions will be numbered identically to those components of FIG. 2, except that a suffix "b" will be used to identify those similar components in FIG. 6.

Label 79 as shown in FIG. 6 is an alternate embodiment of the label that can be used with assembly 10b. The alternate embodiment of the invention as shown in FIG. 6, is that label 79 covers the entire planar cover surface of lid 50b.

Figure 7:
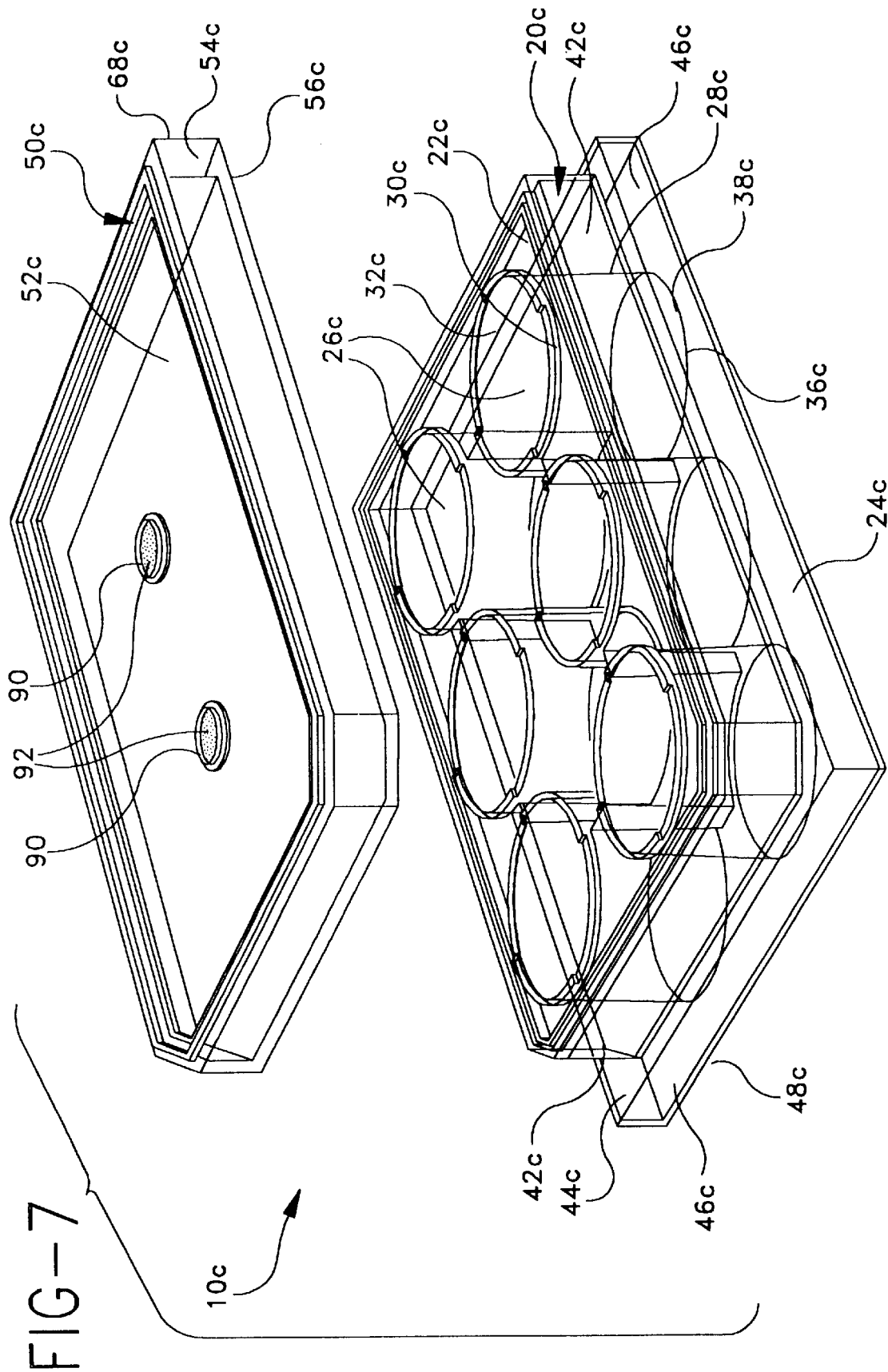
FIG. 7 is a perspective view of an alternate embodiment of the present invention showing more than one orifice in the lid.

An additional embodiment of the invention as shown in FIG. 7 includes many components which are substantially identical to the components of FIG. 2. Accordingly, similar components performing similar functions will be numbered identically to those components of FIG. 2, except that a suffix "c" will be used to identify those similar components in FIG. 7.

Lid 50c as shown in FIG. 7 is an alternate embodiment of the lid that can be used with assembly 10c. The alternate embodiment of the invention as shown in FIG. 7, is that two orifices 90 are located in the planar cover and each has a liquid impermeable membrane 92 associated therewith. Although FIG. 7 only show two orifices, it is well within the purview of the invention to have more than two orifices in the planar cover.

In use, the present invention may be used for culturing cells as follows:
  a. removing the lid from the culture vessel;
  b. depositing a layer of cells on the membrane of the cell insert within the culture vessel;
  c. overlaying the layer of cells with a growth medium;
  d. placing the lid over the plate; and
  e. ventilating the membrane of the cell insert by permitting air access thrusts through the orifice in the lid of the culture vessel by removing or partially removing and re-attaching the label over the orifice.

As practitioners-in-the-art will understand, the culture vessel assembly of the present invention may be comprised of simple moldable parts which may be mass produced from a variety of materials, including, for example, polyethylene, polystyrene, polyethylene terephthalate and polypropylene. As will be understood further by practitioners in the art, materials should be selected which provide a small degree of resiliency for the purpose of providing ease of use for subsequent examination of the developed cultured cells.

What is claimed is:

1. An assembly comprising:
   a test plate comprising a plurality of wells having openings therein for receiving tissue culture media and upstanding sidewall forming an outside border of said plate;
   a lid removably positioned on said plate comprising a substantially planar cover extending over said wells, a skirt surrounding said cover defining a plurality of corners on said cover and extending downwardly in spaced relation with respect to said sidewall of said plate;
   an orifice in said planar cover;
   a gas permeable membrane associated with said orifice; and
   a gas impermeable film removably attached to said cover over said orifice and said gas permeable membrane whereby said film may be fully or partially removed to assist in gas diffusion into and out of said assembly.

2. The assembly of claim 1 wherein said sidewall of said plate comprises a two-step section comprising an upper section and a lower section.

3. The assembly of claim 2 wherein said lower section is stepped from said upper section by an annular shoulder.

4. The assembly of claim 1 wherein said skirt of said lid extends to a position adjacent to, but out of contact with, said annular shoulder of said plate.

5. The assembly of claim 1 wherein said wells are arranged in substantially orthogonal rows and columns.

6. The assembly of claim 1 wherein said plate and said lid are made of transparent plastic.

7. The assembly of claim 1 wherein said test plate further comprises a ledge spaced inwardly from said sidewall of said plate and extending around said plate between said sidewall and said wells wherein said sidewall extends to a position raised above said ledge thereby forming a rim surrounding said ledge.

8. A lid for use in conjunction with a tissue culture plate comprising:
   a substantially planar cover comprising an upper surface and a lower surface;
   a skirt surrounding said cover defining a plurality of corners on said cover and extending downwardly to form sidewalls;
   an orifice in said cover comprising a gas permeable membrane; and
   a gas impermeable film removably attached to said cover over said orifice and said gas permeable membrane whereby said film may be fully or partially removed.

9. The lid of claim 8 wherein said gas impermeable film is a peel-away label.

10. The lid of claim 9 further comprising a plurality of flanges being inwardly spaced from said skirt and extending downwardly from said lower surface of said cover.

11. A device for growing cells or tissue culture in vitro comprising:
   a body comprising an upper surface, a lower surface, a plurality of wells substantially disposed between said upper and lower surface and upstanding sidewall forming an outside border of said body;
   a removable lid, comprising a top wall and a peripheral skirt that extends from said top wall and means for allowing gas diffusion into and out of said device, wherein said means for allowing gas diffusion into and out of said device is an orifice and a gas permeable membrane associated with said orifice; and a gas impermeable film removably attached to said cover over said orifice whereby said film may be partially or fully removed to assist with gas diffusion in the device.

12. The device of claim 11 wherein said sidewall of said body includes a two step section comprising an upper section and a lower section.

13. The device of claim 12 wherein said sidewall of said body further comprises an annular shoulder whereby said lower section is stepped from said upper section by said annular shoulder.

14. A method of culturing cells comprising:
  (a) providing a culture vessel comprising a test plate comprising a plurality of wells having openings therein for receiving tissue culture media and upstanding sidewall forming an outside border of said plate; a lid removably positioned on said plate comprising a substantially planar cover extending over said wells, a skirt surrounding said cover defining a plurality of corners on said cover and extending downwardly in spaced relation with respect to said sidewall of said plate; an orifice in said planar cover; a gas permeable membrane associated with said orifice; and a removable label associated with said orifice to cover said membrane;
  (b) removing said lid from said culture vessel;
  (c) placing a cell insert comprising a membrane within said well of said culture vessel;
  (d) depositing a layer of cells on the membrane of said cell insert within said culture vessel;
  (e) overlaying the layer of cells with a growth medium;
  (f) placing said lid on said plate to cover said wells; and
  (g) ventilating said membrane by permitting air access thrusts through said orifice in said lid of said culture vessel by removing and re-attaching said label over said orifice.

\* \* \* \* \*